United States Patent
Stocks et al.

(10) Patent No.: US 8,287,525 B2
(45) Date of Patent: Oct. 16, 2012

(54) ILLUMINATION DEVICE AND METHOD OF USE FOR OPHTHALMIC SURGERY

(75) Inventors: David John Stocks, Royston (GB); Simon Roderick Grover, Cambridge (GB); Mike Nelson, Bar Hill (GB)

(73) Assignee: Bausch & Lomb Incorporated, Rochester, NY (US)

( * ) Notice: Subject to any disclaimer, the term of this patent is extended or adjusted under 35 U.S.C. 154(b) by 243 days.

(21) Appl. No.: 12/868,777

(22) Filed: Aug. 26, 2010

(65) Prior Publication Data

US 2011/0060319 A1    Mar. 10, 2011

Related U.S. Application Data

(60) Provisional application No. 61/239,936, filed on Sep. 4, 2009.

(51) Int. Cl.
*A61B 18/18* (2006.01)
*G02B 6/36* (2006.01)

(52) U.S. Cl. .................. 606/16; 606/10; 606/4; 385/93; 385/92; 385/88

(58) Field of Classification Search .................... 385/53, 385/88, 92, 93, 94; 606/4, 7, 10, 11, 12, 606/13, 14, 15, 16, 17, 18
See application file for complete search history.

(56) References Cited

U.S. PATENT DOCUMENTS

| | | | |
|---|---|---|---|
| 4,870,952 A | 10/1989 | Martinez | |
| 5,085,492 A | 2/1992 | Kelsoe et al. | 385/60 |
| 5,470,330 A | 11/1995 | Goldenberg et al. | 606/7 |
| 5,738,677 A | 4/1998 | Colvard et al. | 606/4 |
| 7,292,323 B2* | 11/2007 | Artsyukhovich et al. | 356/73.1 |
| 7,402,158 B2* | 7/2008 | Scheller et al. | 606/4 |
| 2008/0287938 A1 | 11/2008 | Scheller et al. | 606/15 |

FOREIGN PATENT DOCUMENTS

| | | |
|---|---|---|
| EP | 0 305 170 | 3/1989 |
| GB | 2 040 495 | 8/1980 |
| WO | WO 2006/053273 | 5/2006 |
| WO | WO 2011028592 A1 * | 3/2011 |

OTHER PUBLICATIONS

International Search Report (PCT/ISA/210) for prepared for PCT/US10/46765, Nov. 22, 2010.*
Written Opinion of the International Search Authority (PCT/ISA/237) for prepared for PCT/US10/46765, Nov. 22, 2010.*
International Preliminary Report on Patentability (PCT/IPEA/409) for prepared for PCT/US10/46765, Aug. 5, 2011.*
International Search Report (PCTISA/210) and Written Opinion (PCT/ISA/237) mailed on Feb. 2, 2011.
Bausch & Lomb Millennium Owner's Manual pp. 1 Sep. 2004.

* cited by examiner

*Primary Examiner* — David N Spector
(74) *Attorney, Agent, or Firm* — Jeffrey B Powers

(57) ABSTRACT

An illumination device for use in an ophthalmic surgical apparatus, the illumination device including a fiber optic having a proximal end and a connector coupled to the fiber optic. The connector includes one or more of (1) a datum surface disposed a predetermined distance from the proximal end to position the proximal end at a predetermined location within the surgical apparatus, (2) a shutter actuation surface configured and arranged to open a shutter in the surgical apparatus when the connector is being connected to the surgical apparatus, and (3) a visual indicator position to provides a visual indication that the connector is fully inserted into the surgical apparatus. The illumination device may be in a combination with an ophthalmic surgical apparatus.

9 Claims, 3 Drawing Sheets

ILLUMINATION DEVICE AND METHOD OF USE FOR OPHTHALMIC SURGERY

CROSS REFERENCE

This application claims the benefit of provisional patent application No. 61/239,936, filed Sep. 4, 2009 and is incorporated herein by reference.

FIELD OF INVENTION

The present invention relates to illumination devices for ophthalmic surgery and methods of use thereof.

BACKGROUND OF THE INVENTION

The need to provide illumination to facilitate performance of ophthalmic surgery in a patient's eye is known. To efficiently and reliably provide such illumination has been difficult, particularly for vitreoretinal surgery. A significant factor in efficient and reliable illumination is coupling of light from a source disposed in a surgical console into a fiber optic of an illumination device. The fiber optic acts as a conduit to deliver the light to a surgical handpiece and into patients' eyes.

In addition to the need of coupling light into the fiber is a need to appropriately dissipate heat generated in the fiber optic when the fiber is exposed to the intense light provided by the source. To date, the problems of coupling light into a fiber and dissipating heat have been addressed by providing a metallic heat sink proximate the end of the fiber and using the heat sink as a connector to the console. In such a configuration, the heat sink is inserted into a port in the console and retained by friction between the heat sink and the console.

SUMMARY

Aspects of the present invention are directed to techniques for enhancing alignment of an end of a fiber optic within an ophthalmic surgical console to provide better coupling of light from a source into the end of the fiber. Other aspects of the invention are directed to a fiber optic connector providing shutter control to control light escaping the console into a surgery room. Yet other aspects of the invention are directed to ensuring proper connection of an illumination device to a surgical console.

An illumination device, according to the exemplary embodiment, is for use in an ophthalmic surgical apparatus. The illumination device includes a fiber optic having a proximal end and a connector coupled to the fiber optic. The connector has a datum surface disposed a predetermined distance from the proximal end. The connector is configured and arranged to connect with the surgical apparatus such that the datum surface positions the proximal end at a predetermined location within the surgical apparatus when the connector is connected to the surgical apparatus.

In one example the connector also includes a heat sink surrounding a portion of the fiber optic. The heat sink is also attached to the connector wherein the fiber optic proximal end is located proximate an end of the heat sink.

In another example the connector is adapted to fit into and move a collar within a port in the surgical apparatus upon insertion of the connector into the port, thereby opening a shutter within the surgical apparatus to transmit light through the fiber optic.

In still another example the connector includes a visual indicator disposed a predetermined distance from the proximal end such that a position of the visual indicator provides a visual indication that the connector is fully inserted into the surgical apparatus.

A method of coupling an illumination device to an ophthalmic surgical apparatus comprising a light source is also accomplished by providing a fiber optic having a proximal end, providing a connector with a datum surface coupled to the fiber optic; and coupling the connector to the surgical apparatus such that the proximal end is positioned at a predetermined location relative to the light source by interference of the datum surface with a surface of the surgical apparatus, thereby transmitting light from the light source into the proximal end and through the fiber optic.

Some examples also include a connector coupled to the fiber optic where the connector has a shutter actuation surface configured and arranged to open a shutter in the surgical apparatus when the connector is being connected to the surgical apparatus and to maintain the shutter in an open position when the connector is coupled to the surgical apparatus such that light from the light source is transmitted into the proximal end and through the fiber optic.

BRIEF DESCRIPTION OF THE DRAWINGS

Illustrative, non-limiting embodiments of the present invention will be described by way of example with reference to the accompanying drawings, in which the same reference number is used to designate the same or similar components in different figures, and in which.

DETAILED DESCRIPTION

Figure 1A:
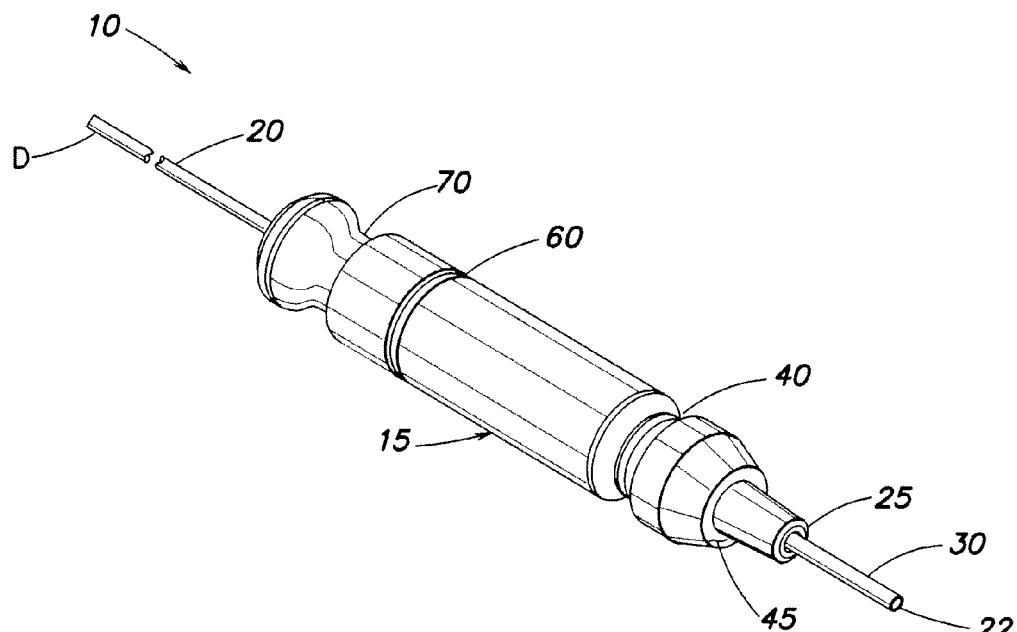
FIG. 1A is a schematic illustration of an example of an illumination device for use in an ophthalmic surgical apparatus according to aspects of the present invention.
Figure 1B:
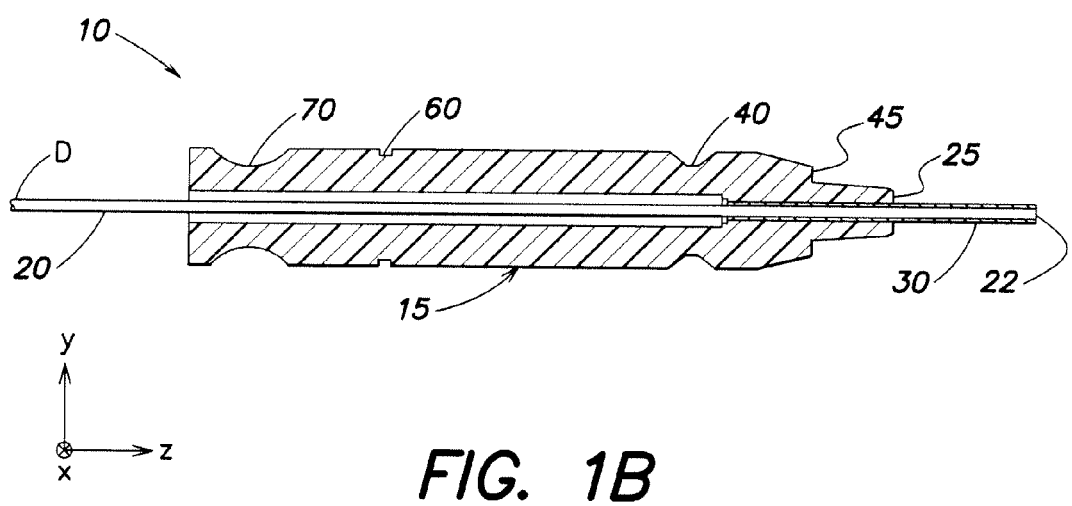
FIG. 1B is a schematic cross-sectional illustration of an example of an illumination device for use in an ophthalmic surgical apparatus according to aspects of the present invention.

FIG. 1A is a schematic illustration of an example of an illumination device 10 for use in an ophthalmic surgical apparatus according to aspects of the present invention, and FIG. 1B is a schematic, cross-sectional illustration of an example of an illumination device 10 for use in an ophthalmic surgical apparatus according to aspects of the present invention. Aspects of the invention will now be described with reference to both FIGS. 1A and 1B.

Illumination device 10 comprises a fiber optic 20, a connector 15 and a heat sink 30. It will be appreciated that an ophthalmic surgical handpiece (not shown) is provided on the distal end D of the illumination device from which light is projected into a patient's eye to permit observation by surgical staff, during surgery. The handpiece can have any suitable, known or yet to be developed configuration. In embodiments having a heat sink 30 surrounding a portion of the fiber optic, the heat sink is also attached to the connector 15 so that the fiber optic proximal end 22 is located proximate an end of the heat sink 30.

Fiber optic 20 has a proximal end 22. The fiber optic is positioned with the proximal end 22 exposed to light from a source (discussed below) which is disposed within the surgical console such that light can be propagated through the fiber to distal end D. It will be appreciated that proper and consistent positioning of the proximal end 22 is desirable for efficient and reliable illumination of a patient's eyes. In particular, it is desirable that such positioning be achieved when a used device 10 is removed and a new device 10 is connected to a console numerous times.

To facilitate suitable positioning of the proximal end 22, according to aspects of the present invention, fiber optic 20 is coupled to connector 15 which comprises a datum surface 25 that is disposed a predetermined distance from the proximal end 22. It will be appreciated that if fiber optic 20 is maintained at a fixed location within the connector, as discussed in greater detail below, by interfacing datum surface with a datum surface within the console, the positioning of the proximal end in the z-direction can be achieved. It will also be appreciated that by maintaining fiber optic 20 in intimate contact with the connector the positioning of the proximal end 22 in the x-direction and the y-direction can also be achieved. Accordingly, the connector 15 is configured and arranged to connect with the ophthalmic surgical apparatus such that datum surface 25 positions proximal end 22 at a predetermined location within a surgical apparatus (e.g., within a console) when the connector is connected to the surgical apparatus. It will be appreciated that it is typically advantageous that the datum surface 25 be located near the proximal end of connector 15 (i.e., relatively near the fiber proximal end 22) to reduce stack-up of tolerances which would limit the precision with which proximal end 22 can be positioned. In the illustrated embodiment, datum surface 25 is illustrated as a simple vertical surface; however, more complicated shapes can be used.

Connector 15 may be manufactured from any suitable rigid material. Typically the material is a heat insulator to prevent transfer of heat generated by the fiber from reaching housing or an operator's hand. For example, the connector may be made of an acetal homopolymer such as Delrin® available from the Dupont Corporation.

To facilitate control of light emitted from the console by the source the connector 15 comprises a shutter actuation surface 45. Interaction of shutter actuation surface 45 with a shutter in the surgical apparatus is discussed in greater detail below. It will be appreciated that the shutter actuation surface 45 causes the shutter to open, when connector 15 is being connected to the surgical apparatus. In addition, the shutter remains in an open position when the connector 15 is coupled to the surgical apparatus such that light from the light source is transmitted into the proximal end 22 and through fiber optic 20. Such a configuration provides advantages over a gravity operated shutter, which needs to be manually moved out of the way prior to insertion of the illumination device.

In some embodiments, the connector comprises a visual indicator 60 disposed a predetermined distance from the proximal end. The connector 15 is configured and arranged to connect with the surgical apparatus such that the visual indicator 60 position provides a visual indication that the connector 15 is fully inserted into the surgical apparatus. In the illustrated embodiment, when the connector 15 is fully inserted, the visual indicator 60 is immediately adjacent an outer surface 62 of a housing of the surgical apparatus 64 (see FIG. 3). In the illustrated embodiment, the visual indicator 60 is represented by a groove. Of course, visual indicator 60 may assume other forms, for example, a raised ridge, and/or a contrasting color, or other suitable visible feature.

The illumination device 10 may further comprise a heat sink 30 coupled to fiber optic 20 at a location proximate the proximal end 22. In embodiments where a heat sink is included, it is typically desirable to maintain the fiber in intimate contact with the heat sink to facilitate precise positioning of proximal end 22 in the x-direction and the y-direction. That is heat sink 30 is typically a relatively rigid metallic tube or needle that has a larger enough lumen to allow easy insertion of an optic fiber during manufacturing but where the lumen is small enough that the fiber proximal end 22 is able to be reliably located in the x and y directions within the tolerances of the design requirements. In embodiments including a heat sink, it is also typically desirable to maintain the connector in intimate contact with the heat sink to further facilitate precise positioning of the proximal end.

It will be appreciated that an embodiment according to aspects of the present invention can be provided with one or more of a datum surface, a shutter actuation surface and a visual indicator.

Figure 2:
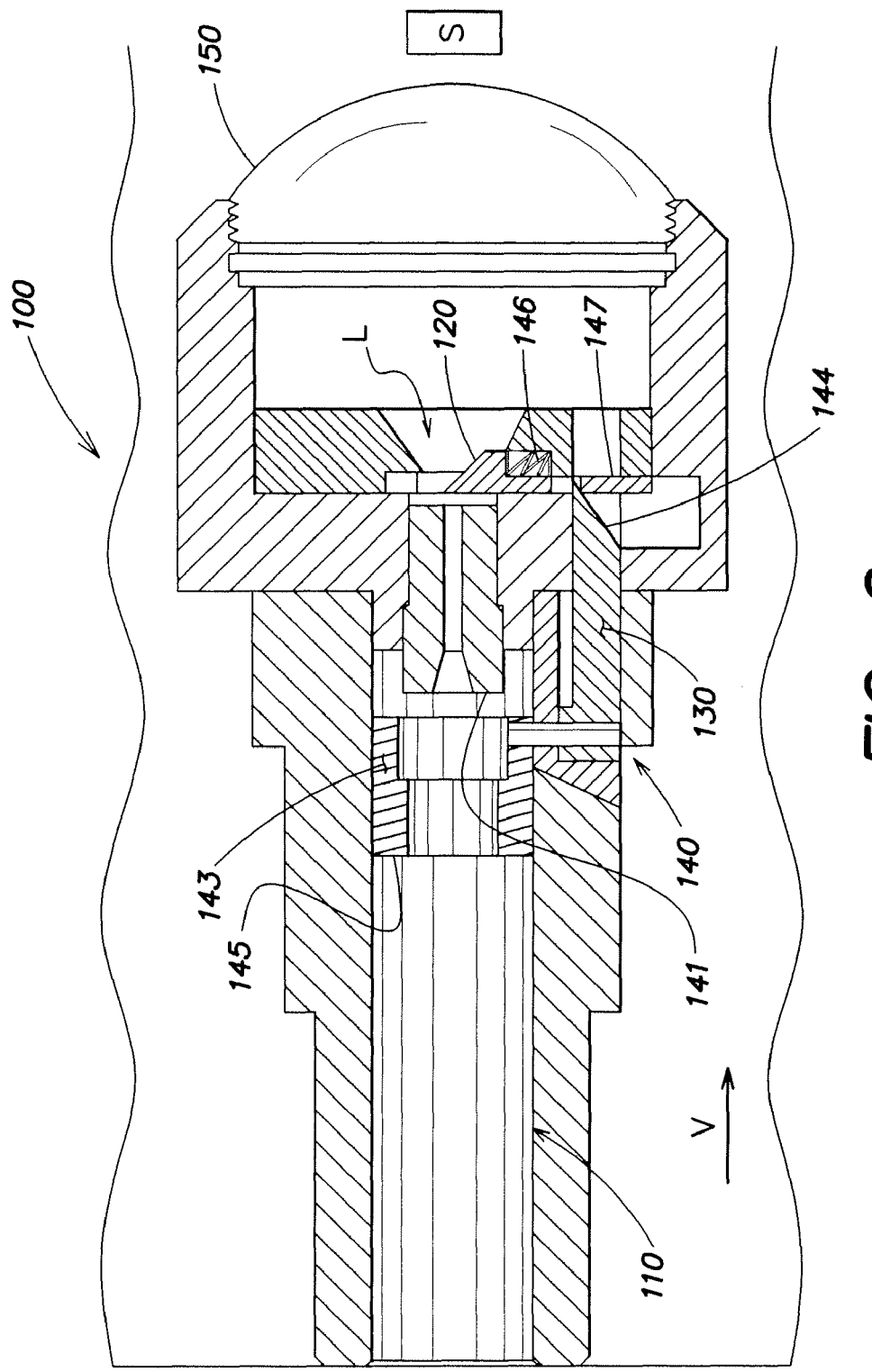
FIG. 2 is a schematic, partial cross-sectional illustration of an example of an ophthalmic console including a port for connecting an illumination device.
Figure 3:
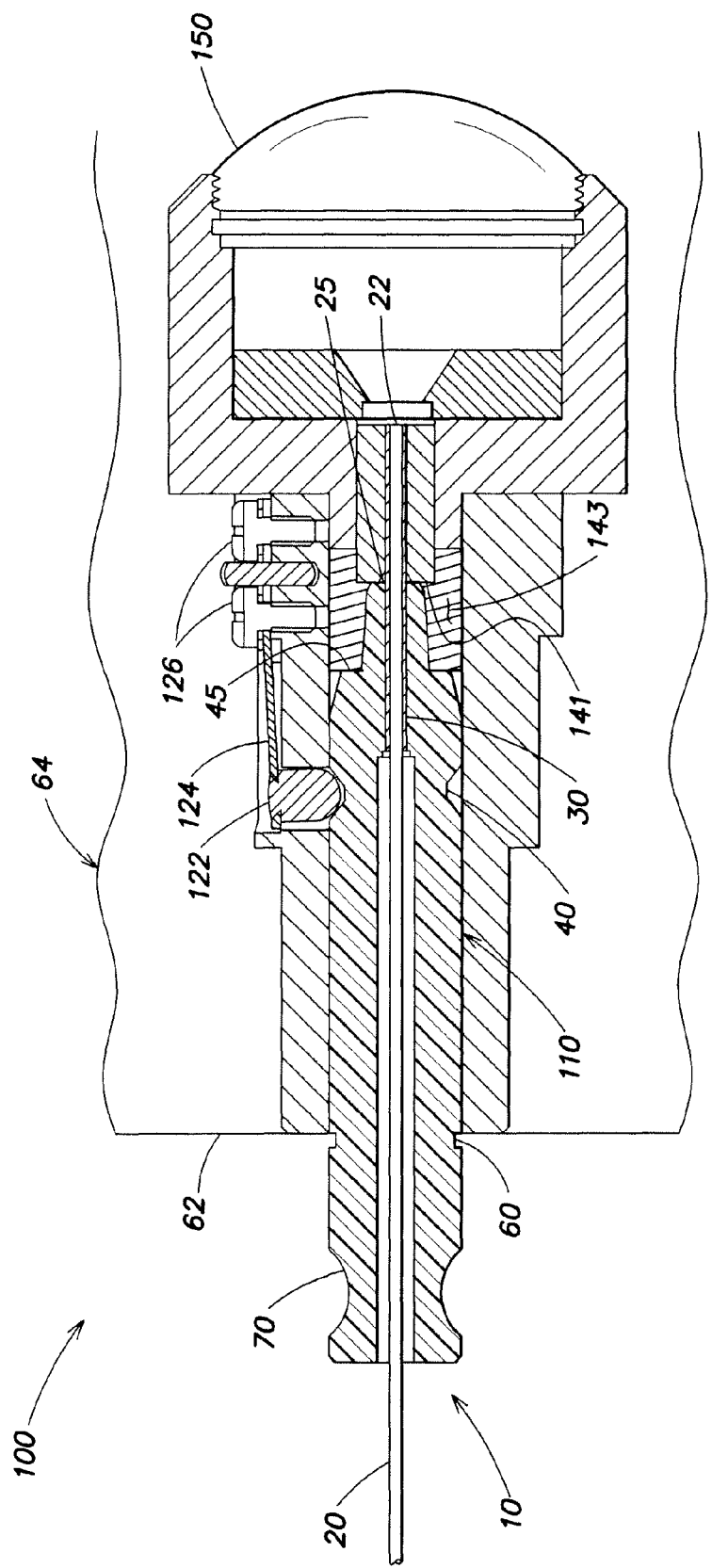
FIG. 3 is a schematic, partial cross-sectional illustration of an example of an ophthalmic console including a port having an illumination device connected thereto.

FIG. 2 is a schematic, partial cross-sectional illustration of an example of an ophthalmic surgical console 100 including a port 110 for connecting illumination device 10. FIG. 3 is a schematic, partial cross-sectional illustration of an example of an ophthalmic surgical console 100 including a port 110 having illumination device 10 connected thereto. FIGS. 2 and 3 will be referenced together when describing aspects of the present invention below.

Console 100 contains a light source S. The light source is positioned to be capable of projecting light though port 110. The light source may comprise any suitable light emitting apparatus (e.g., an incandescent lamp or an LED). Console 100 may be an ophthalmic surgical system such as those known in the art that contains apparatus in accordance with the present examples or console 100 could be a stand alone ophthalmic illuminator, similar to those known in the art, and incorporates apparatus in accordance with the present examples.

As described above with reference to FIG. 1B, the illumination device 10 comprises a fiber optic 20 having a proximal end 22 through which light enters illumination device 10, and a connector 15 coupled to the fiber optic 20. The connector 15 is connected with the surgical console 100. The connector 15 is configured and arranged such that datum surface 25 positions the proximal end 22 at a predetermined location relative to light source S. Typically, a pair of datum surfaces (e.g., one on a console and one on an illumination device) achieves alignment. By this technique, mechanical positioning between a pair of datum surfaces can achieve and maintain alignment within a predetermined operating range, depending on the requirements of the amount of light needed to be captured by fiber optic 20. For example, the datum surface 25 when abutting surface 141 (see FIGS. 2 and 3) may operate to position proximal end 22 at a location proximate a focal point of lens 150 or at another position to capture a particular amount of light from the source S.

In the illustrated embodiment, port 110 is moveable in direction V upon insertion of an illumination device 10 into the port 110 to operate an illumination shutter 120. Illumination shutter 120 controls whether light is transmitted through port 110. The shutter has an open position in which the shutter permits light to be transmitted through the port, and a closed position (shutter 120 is shown in the closed position in FIG. 2) in which the shutter 120 blocks transmission of light. A biasing feature 146 biases the shutter in the closed position. Biasing feature 146 in the present example is simply a spring arm that causes shutter 120 to return to the closed position when illumination device 10 is removed; however, biasing feature 146 may comprise any structure that ensures that shutter 120 blocks light when an illumination device 10 is not connected to console 100.

In the illustrated embodiment, a shutter actuation device 140 includes a shutter collar 143 that slides within port 110. Shutter collar 143 is connected to an arm 130. Arm 130 has a tapered edge 144 that, when moved in direction V as an illumination device 10 is inserted, forces the shutter 120 downward (i.e., overcoming the biasing feature) via contact with structure 147, permitting light L to pass into proximal end 22.

Shutter actuation surface 45 is configured and arranged to open shutter 120 in the console when the connector 15 is being connected to the console. In the illustrated embodiment, shutter actuation surface 45 is sized and shaped to interfere with surface 145 of shutter collar 143 in the port 110 such that, upon insertion of connector 15 into port 110, actuation device 140 opens shutter 120 in the manner described above.

Shutter actuation surface 45 is configured to maintain the shutter in an open position such that light from the light source S is transmitted into the proximal end 22 and through the fiber 20 so long as connector 15 is connected within port 110.

In some embodiments, one or more features may be present to provide further retention of illumination device 10 beyond that which may be provided by friction between the connector 15 and the port 110. In the illustrated embodiment, region or groove 40 having a reduced diameter is provided on the connector 15 and a detent is provided on the surgical apparatus to maintain connector in operative position during use. For example, in the illustrated embodiment, the detent comprises a plunger 122 biased using a flexible bar 124 that is attached to the console by fasteners 126.

It may also be advantageous that surfaces of the connector 15 be beveled to facilitate insertion of the connector 15 into port 110. In some embodiments, it is advantageous to provide features that facilitate removal of the connector from the port such as indent 70 shaped to permit a user's fingers to be inserted therein so as to reliably grasp the connector.

Having thus described the inventive concepts and a number of exemplary embodiments, it will be apparent to those skilled in the art that the invention may be implemented in various ways, and that modifications and improvements will readily occur to such persons. Thus, the embodiments are not intended to be limiting and presented by way of example only. The invention is limited only as required by the following claims and equivalents thereto.

What is claimed is:

1. An illumination device for use in an ophthalmic surgical apparatus, the illumination device comprising:
    a fiber optic having a proximal end;
    a connector coupled to the fiber optic comprising a datum surface disposed a predetermined distance from the proximal end, the connector configured and arranged to connect with the surgical apparatus such that the datum surface positions the proximal end at a predetermined location within the surgical apparatus when the connector is connected to the surgical apparatus; and
    wherein the illumination device is adapted to fit into and move a collar within a port in the surgical apparatus upon insertion of the connector into the port, thereby opening a shutter within the surgical apparatus to transmit light through the fiber optic.

2. The illumination device of claim 1, further comprising a heat sink surrounding a portion of the fiber optic and attached to the connector wherein the fiber optic proximal end is located proximate an end of the heat sink.

3. An illumination device in a combination with ophthalmic surgical apparatus comprising a light source, the combination comprising:
    a fiber optic having a proximal end;
    a connector coupled to the fiber optic comprising a datum surface disposed a predetermined distance from the proximal end, the connector datum surface abutting a surgical apparatus surface such that the proximal end is positioned at a predetermined location relative to the light source; and
    wherein the illumination device is adapted to fit into and move a collar within a port in the surgical apparatus upon insertion of the connector into the port, thereby opening a shutter within the surgical apparatus to transmit light through the fiber optic.

4. The combination of claim 3, further comprising a heat sink surrounding a portion of the fiber optic and attached to the connector wherein the fiber optic proximal end is located proximate an end of the heat sink.

5. The illumination device of claim 3, wherein the connector further comprises a visual indicator disposed a predetermined distance from the proximal end, the connector configured and arranged to connect with the surgical apparatus such that a position of the visual indicator provides a visual indication that the connector is fully inserted into the surgical apparatus.

6. An illumination device for use in an ophthalmic surgical apparatus comprising a light source, the illumination device comprising:
    a fiber optic having a proximal end; and
    a connector coupled to the fiber optic comprising a datum surface disposed a predetermined distance from the proximal end and a shutter actuation surface, the connector (i) configured and arranged to connect with the surgical apparatus such that the datum surface positions the proximal end at a predetermined location relative to the light source apparatus when the connector is coupled to the surgical apparatus and (ii) configured and arranged such that the shutter actuation surface opens a shutter when the connector is being coupled to the surgical apparatus and maintains the shutter in an open position when the connector is coupled to the surgical apparatus such that light from the light source is transmitted into the proximal end and through the fiber optic.

7. The illumination device of claim 6, further comprising a heat sink surrounding a portion of the fiber optic and attached to the connector wherein the fiber optic proximal end is located proximate an end of the heat sink.

8. The illumination device of claim 6, wherein the illumination device is adapted to fit into a port in the surgical apparatus and interfere with a collar within a port in the surgical apparatus upon insertion of the connector into the port, thereby opening a shutter within the surgical apparatus to transmit light through the fiber optic.

9. The illumination device of claim 6, wherein the connector further comprises a visual indicator disposed a predetermined distance from the proximal end, the connector configured and arranged to connect with the surgical apparatus such that a position of the visual indicator provides a visual indication that the connector is fully inserted into the surgical apparatus.

* * * * *